(12) United States Patent
Helms et al.

(10) Patent No.: US 6,524,286 B1
(45) Date of Patent: *Feb. 25, 2003

(54) MEDICAL APPLICATION SYSTEM FOR ANIMALS

(76) Inventors: Gordon O. Helms, HC65 Box 16, Reva, SD (US) 57651; Jeff Thompson, HC65 Box 15, Reva, SD (US) 57651

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/276,106

(22) Filed: Mar. 25, 1999

(51) Int. Cl.[7] ................................................. A61M 35/00
(52) U.S. Cl. .......................... 604/289; 606/116; 604/19
(58) Field of Search ............................ 604/57, 68, 19, 604/69, 70, 71, 289–290; 124/74, 49, 76, 67, 45; 428/35.7, 34.1, 36.92; 606/116, 117; 102/501, 502; 42/10, 11, 15–17, 29, 31, 33, 34, 35, 6, 49.01; D22/100, 101, 103, 115, 116

(56) References Cited

U.S. PATENT DOCUMENTS

| | | | | |
|---|---|---|---|---|
| 993,023 A | | 5/1911 | Burgsmuller | |
| 1,135,703 A | * | 4/1915 | Lasares | 124/27 |
| 1,695,228 A | | 12/1928 | Bradner et al. | |
| 2,348,337 A | | 5/1944 | Francis | |
| 2,554,116 A | * | 5/1951 | Monner | 124/74 |
| 2,640,476 A | * | 6/1953 | Spink | 124/74 |
| 2,920,566 A | | 1/1960 | Barker | |
| 3,003,418 A | | 10/1961 | Young | |
| 3,701,533 A | | 10/1972 | Palmer | |
| 3,745,682 A | | 7/1973 | Waldeisen | |
| 3,788,298 A | * | 1/1974 | Hale | 124/11 R |
| 3,861,943 A | * | 1/1975 | Grainger | 117/37 |
| 3,911,824 A | | 10/1975 | Barr et al. | |
| 3,948,263 A | | 4/1976 | Drake, Jr. et al. | |
| 3,980,023 A | | 9/1976 | Misevich | |
| 3,982,536 A | | 9/1976 | Krogseng et al. | |
| 4,020,181 A | * | 4/1977 | Blackman | 424/305 |
| 4,266,477 A | * | 5/1981 | Ackley | 101/40 |
| 4,395,259 A | | 7/1983 | Prestele et al. | |
| 4,449,982 A | | 5/1984 | Gould, III | |
| 4,609,403 A | * | 9/1986 | Wittwer et al. | 106/122 |
| 4,664,664 A | * | 5/1987 | Drake, Jr. | 604/891 |
| 4,682,546 A | | 7/1987 | Chovich | |
| 4,834,059 A | * | 5/1989 | Moorhouse et al. | 124/67 |
| 4,918,085 A | * | 4/1990 | D'Silva et al. | 514/407 |
| 5,009,164 A | | 4/1991 | Grinberg | |
| 5,254,379 A | * | 10/1993 | Kotsiopoulos et al. | 428/35.7 |
| 5,353,712 A | * | 10/1994 | Olson | 102/513 |
| 5,383,442 A | * | 1/1995 | Tippmann | 124/76 |
| 5,394,980 A | * | 3/1995 | Tsai | 206/63.5 |
| D359,529 S | | 6/1995 | Nguyen | |
| 5,450,795 A | * | 9/1995 | Adelman | 102/444 |
| 5,503,137 A | * | 4/1996 | Fusco | 124/72 |
| 5,505,188 A | * | 4/1996 | Williams | 124/74 |
| 5,639,526 A | | 6/1997 | Kotsiopoulos et al. | |
| 5,876,995 A | * | 3/1999 | Bryan | 435/189 |
| 6,145,441 A | * | 11/2000 | Woodall et al. | 102/502 |
| 6,223,658 B1 | * | 5/2001 | Rosa et al. | 102/501 |
| 6,393,992 B1 | * | 5/2002 | Vasel et al. | 102/502 |

\* cited by examiner

*Primary Examiner*—Brian L. Casler
*Assistant Examiner*—Jennifer Maynard

(57) ABSTRACT

A medical application system and method for animals for delivering topical medication to the skin of an animal includes a propulsion device and a frangible capsule containing topical medication in liquid form. In a preferred embodiment the medication is an insecticide and is mixed with an oil based paint. In an alternate embodiment for medicating sheep the liquid is preferably a water based paint to prevent staining of the wool. It is also preferred that the propulsion device be a pump style pellet gun for allowing adjustment of the propulsion force provided to the capsule such that the capsule will impact the animal with sufficient force to break the capsule without harming the animal. In a most preferred embodiment, the capsule further contains a pellet for facilitating breakage of the capsule when the capsule impacts the animal.

3 Claims, 3 Drawing Sheets

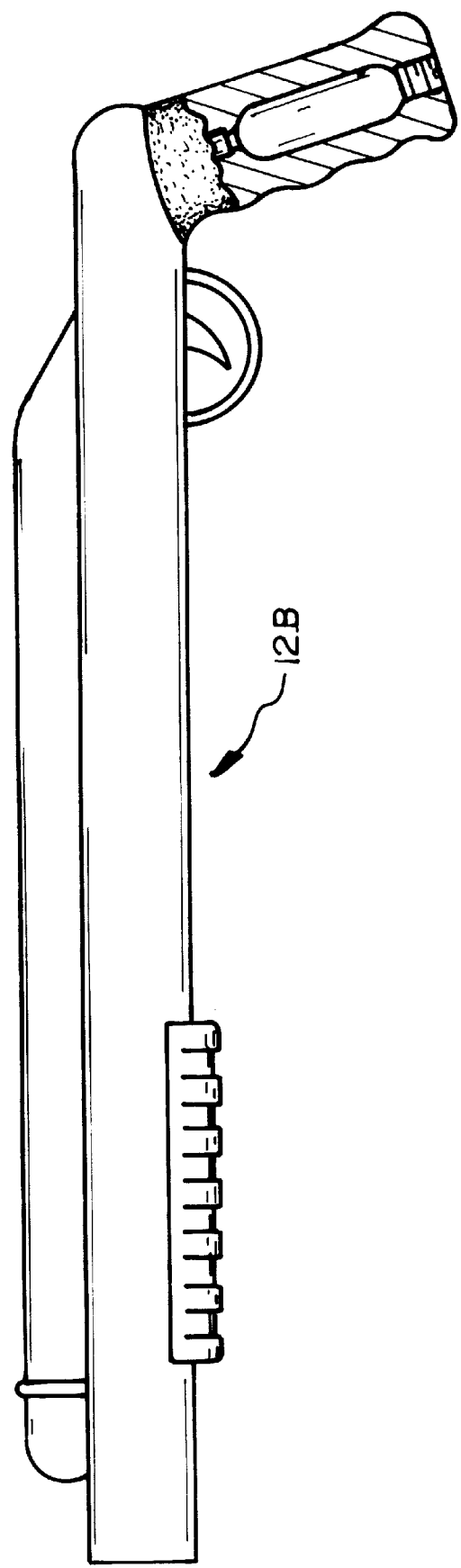

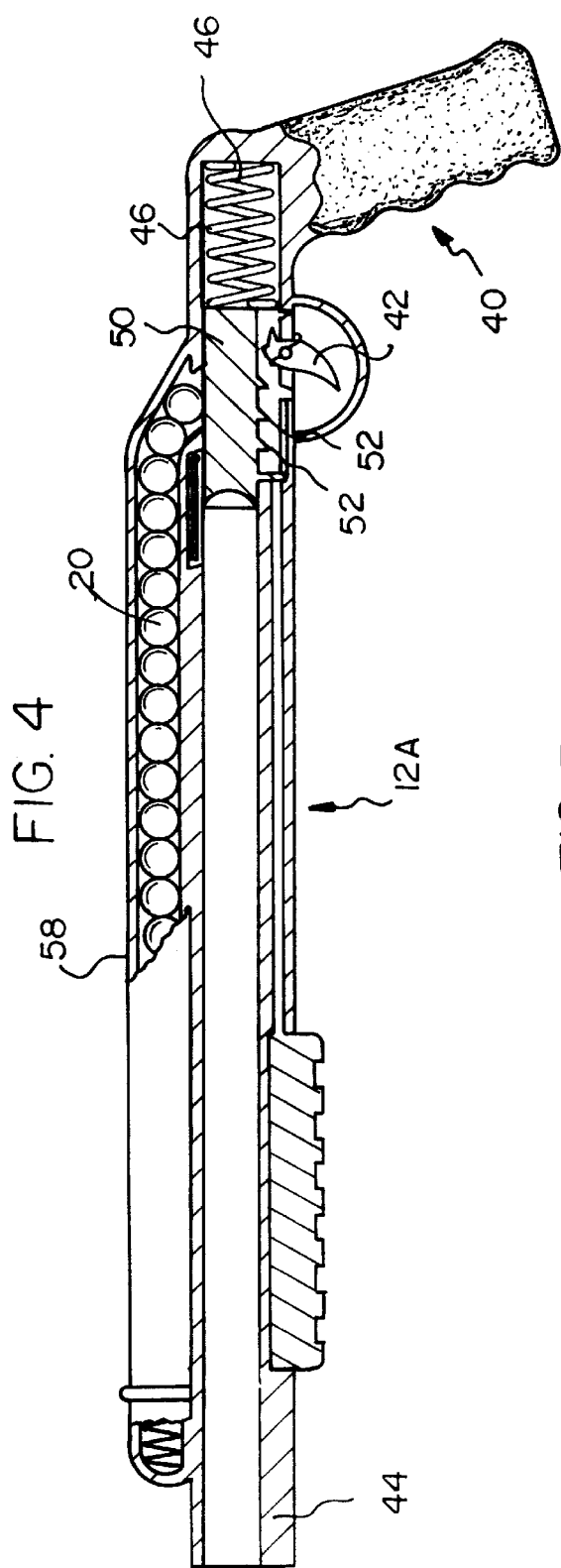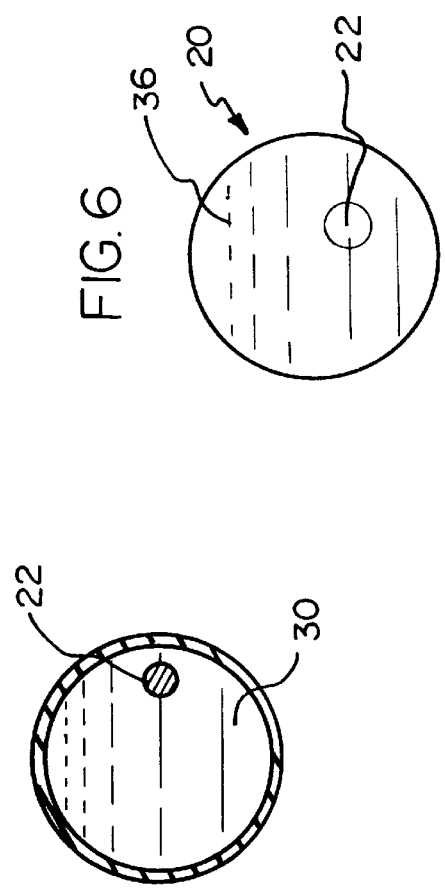

MEDICAL APPLICATION SYSTEM FOR ANIMALS

BACKGROUND OF THE INVENTION

1. Field of the Invention

The present invention relates to medical application systems and more particularly pertains to a new medical application system for animals for delivering topical medication to the skin of an animal.

2. Description of the Prior Art

The use of medical application systems is known in the prior art. More specifically, medical application systems heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 4,449,982; 4,682,546; 993,023; 3,948,263; 3,982,536; 3,980,023; 1,695,228; 4,395,259; 2,348,337; 3,911,824; 2,920,566; 3,745,682; 3,701,533; 5,639,526; 5,009,164; 3,003,418; 5,353,712; and U.S. Pat. No. Des. 359,529.

While these devices fulfill their respective, particular objectives and requirements, the aforementioned patents do not disclose a medical application system for animals. The inventive device includes a propulsion device and a frangible capsule containing topical medication mixed with a liquid.

In these respects, the medical application system for animals according to the present invention substantially departs from the conventional concepts and designs of the prior art, and in so doing provides an apparatus primarily developed for the purpose of delivering topical medication to the skin of an animal.

SUMMARY OF THE INVENTION

In view of the foregoing disadvantages inherent in the known types of medical application systems now present in the prior art, the present invention provides a new medical application system for animals construction wherein the same can be utilized for delivering topical medication to the skin of an animal.

The general purpose of the present invention, which will be described subsequently in greater detail, is to provide a new medical application system for animals apparatus and method which has many of the advantages of the medical application systems mentioned heretofore and many novel features that result in a new medical application system for animals which is not anticipated, rendered obvious, suggested, or even implied by any of the prior art medical application systems, either alone or in any combination thereof.

To attain this, the present invention generally comprises a propulsion device and a frangible capsule containing topical medication and a liquid.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new medical application system for animals apparatus and method which has many of the advantages of the medical application systems mentioned heretofore and many novel features that result in a new medical application system for animals which is not anticipated, rendered obvious, suggested, or even implied by any of the prior art medical application systems, either alone or in any combination thereof.

It is another object of the present invention to provide a new medical application system for animals that may be easily and efficiently manufactured and marketed.

It is a further object of the present invention to provide a new medical application system for animals which is of a durable and reliable construction.

An even further object of the present invention is to provide a new medical application system for animals that is susceptible of a low cost of manufacture with regard to both materials and labor, and which accordingly is then susceptible of low prices of sale to the consuming public, thereby making such medical application system for animals economically available to the buying public.

Still yet another object of the present invention is to provide a new medical application system for animals which provides in the apparatuses and methods of the prior art some of the advantages thereof, while simultaneously overcoming some of the disadvantages normally associated therewith.

Still another object of the present invention is to provide a new medical application system for animals for delivering topical medication to the skin of an animal.

Yet another object of the present invention is to provide a new medical application system for animals which includes a propulsion device and a frangible capsule containing topical medication in liquid form.

Still yet another object of the present invention is to provide a new medical application system for animals that can be used for medicating livestock including cattle, buffalo, swine, horses, sheep, goats, or any other livestock typically raised.

Wherein it has been found that typical processes of applying wormer to livestock that include shuttling the animals through a chute traumatizes the animal resulting in a typical loss of three days of weight gain when in a feedlot system, even still another object of the present invention is to provide a new medical application system for animals that reduces trauma to the animals by allowing the medication of a herd of animals without having to send the animals through a chute.

Yet even another object of the invention is to provide an economical method for medicating animals that simultaneously provides a temporary mark on the animal when a dye or paint is introduced into the liquid contained within the frangible capsule thus preventing overdoses.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is a side view of an alternate embodiment of the pellet gun.

FIG. 4 is a cross-sectional view of the present invention taken along line 4—4 in FIG. 2.

FIG. 5 is a cross sectional view of the capsule taken along line 5—5 of FIG. 1.

FIG. 6 is a perspective view of an alternate embodiment of the capsule.

DESCRIPTION OF THE PREFERRED EMBODIMENT

Figure 1:
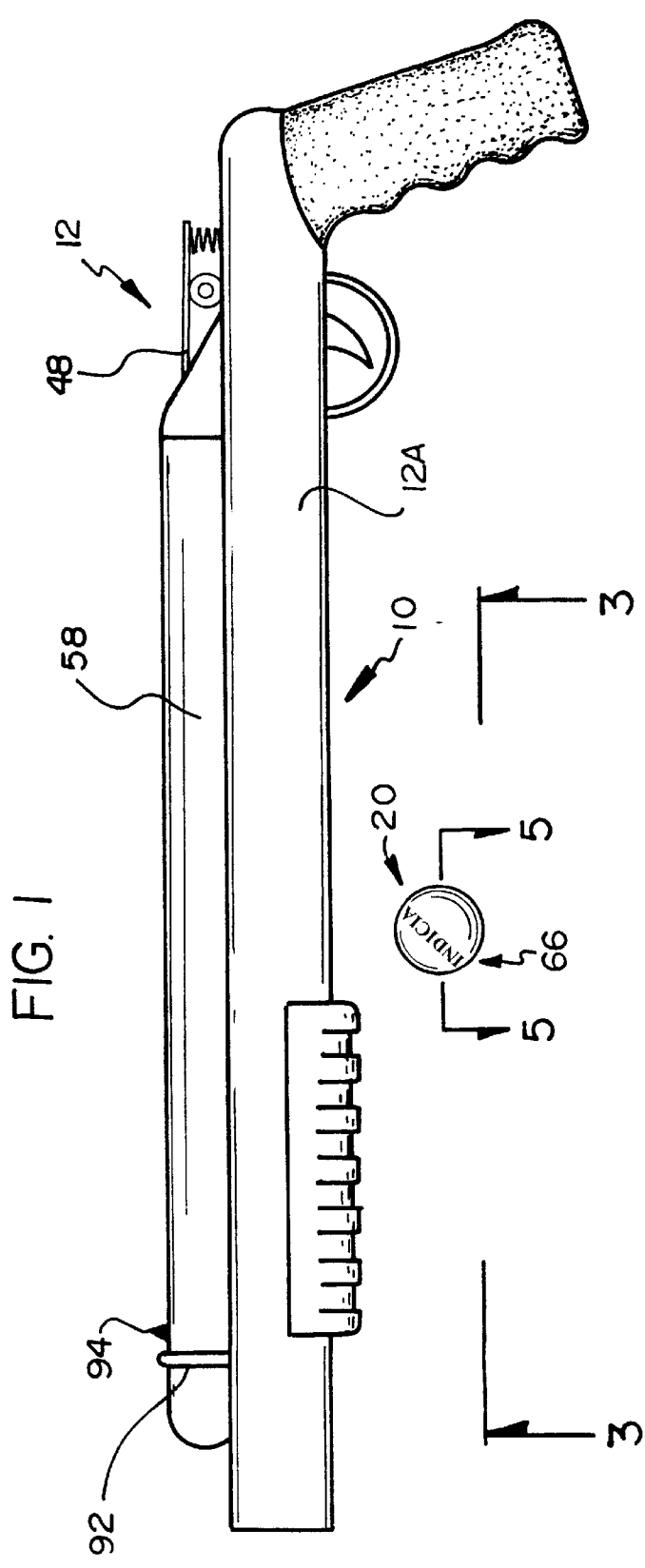
FIG. 1 is a side view of a pellet gun and capsule used for the medical application system for animals according to the present invention.
Figure 3:
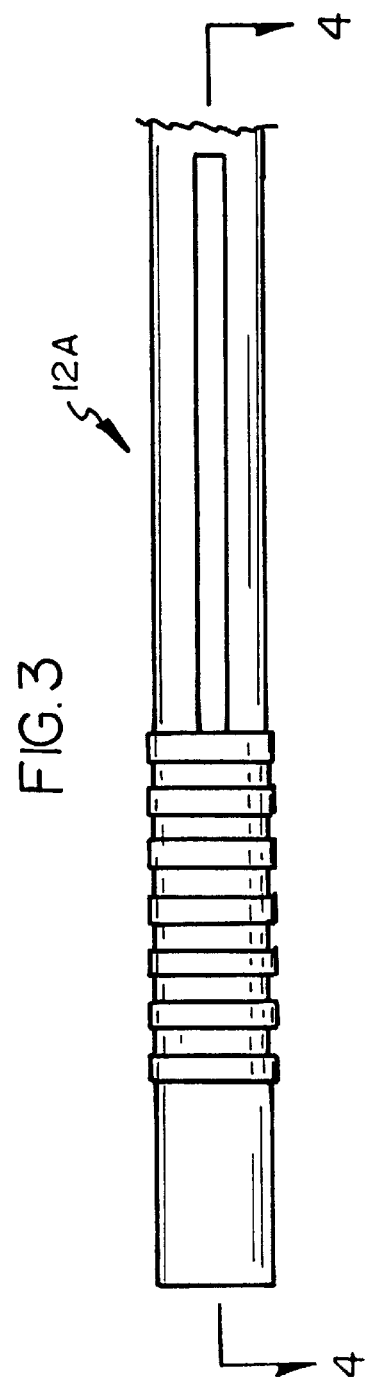
FIG. 3 is a bottom view of the pump action pellet gun.

With reference now to the drawings, and in particular to FIGS. 1 through 6 thereof, a new medical application system for animals embodying the principles and concepts of the present invention and generally designated by the reference numeral 10 will be described.

As best illustrated in FIGS. 1 through 6, the medical application system for animals 10 generally comprises a pellet gun 12, a 70 caliber frangible capsule 20 containing an animal medication 30 in liquid form.

The capsule 20 is positionable within the pellet gun 12 such that the capsule 20 is ejectable from the pellet gun 12 such that the capsule 20 breaks upon impacting the animal whereby the medication 30 is topically delivered to the animal. Most preferably, a pellet 22 is positioned within the frangible capsule 20 both for facilitating breakage of the capsule 20 when the capsule 20 strikes a surface and for agitation of the medication within the capsule to facilitate even distribution of the medication to the skin of the animal for better absorption of the medication by the animal.

The medication 30 is mixed with a coloring agent 36, the coloring agent 36 is designed for marking the animal when the capsule 20 breaks upon impacting the animal for facilitating the prevention of delivering multiple doses of medication to a single animal. The coloring agent 36 is most preferably an oil based paint designed for prevention of the premature removal of the medication 32 from the skin of the animal by rain. Alternately, a water based paint is used and designed for facilitating the removal of the coloring agent from the animal to prevent permanent staining of the animals coat. This is particularly preferred for the medication of sheep to prevent staining of the wool prior to shearing.

The pellet gun 12 is preferably a pump action pellet gun 12A for allowing adjustment of the propulsion force provided to the capsule 20 such that the capsule 20 will impact the animal with sufficient force to break the capsule 20 upon impact without harming the animal. Thus each animal in a herd or group can be safely medicated from varying distances whereby a number of animals can be medicated from one position. Alternately, a pellet gun of the type utilizing a gas cartridge 12B can be used but a minimum distance from the animal to be medicated is necessary to minimize trauma and potential damage to the animal.

The capsule 20 preferably includes a transparent shell 24 to expose the color of the coloring agent 36. The color of the coloring agent within each capsule is associated with a pre-determined dosage of medication for providing a visual indication of the dosage level and facilitating the prevention of overmedicating an animal. Alternately, the capsule 20 can be constructed of an opaque material and colored to indicate an associated dosage level of medication within the capsule 20. Lettering or numbering 66 can also be employed to differentiate dosages for those unable to distinguish colors visually.

Although any topical medication is applicable using the present inventive system and method, the preferred use is for the application of insecticides to prevent worms, flies and lice.

The pellet gun 12B preferably comprises a handle portion 40 having a trigger mechanism 42. A barrel 44 extends from the handle portion 40 and a spring mechanism 46 is positioned within a first end of the barrel 44 proximate the handle portion 40.

A plurality of protrusions 52 extend from a slide member 50. Each protrusion 52 being for engaging the trigger mechanism 42 such that the spring mechanism 46 is compressed. A slide grip 54 is coupled to the barrel 44 for moving the slide member 50 into engagement with the trigger mechanism 42 such that a selected one of the protrusions 52 is engaged to the trigger mechanism 42 whereby a selectable amount of compression of the spring mechanism 46 is achieved.

A removable capsule chamber 58 is coupled to the barrel 44 by insertion of the capsule chamber through a loop 92 proximate one end of the capsule chamber. The capsule chamber includes a shoulder 94 for abutting the loop to facilitate holding the capsule chamber 58 in position. A clip 48 for holding the opposite end of the capsule chamber 58 is positioned proximate the handle portion 40. The capsule chamber 58 is designed for holding the plurality of capsules 20 within an interior of the capsule chamber 58. The interior of the capsule chamber 58 is in communication with an interior of the barrel 44 such that one of the capsules 20 is delivered to the barrel 44 such that the capsule 20 abuts the slide member 50 when the slide member 50 is moved into engagement with the trigger mechanism 42.

The trigger mechanism 42 is disengagable from the slide member 50 whereby the capsule 20 is propelled out of the barrel 44.

In use, a plurality of capsules 20 are loaded into the pellet gun 12. The gun is aimed at the animal to be medicated and one of the plurality of capsules is ejected from the pellet gun such that the capsule impacts the animal whereby the capsule breaks open to dispense the medication onto the skin of the animal.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A medication delivery system for medicating an animal comprising:
    a propulsion device;
    a frangible capsule containing a topically applicable animal medication in liquid form;
    the capsule being positionable within the propulsion device such that the capsule is ejectable from the propulsion device such that the capsule breaks upon impacting the animal whereby the medication is topically delivered to the animal;
    said frangible capsule being generally spheroid for preventing implantation of said frangible capsule into the animal upon impacting the animal;
    wherein the propulsion device comprises a pellet gun;
    wherein the pellet gun comprises
        a handle portion having a trigger mechanism;
        a barrel extending from the handle portion;
        a spring mechanism positioned within a first end of the barrel proximate the handle portion;
        a slide member having a plurality of protrusions extending therefrom, each protrusion being for engaging the trigger mechanism such that the spring mechanism is compressed;
        a slide grip coupled to the barrel for moving the slide member into engagement with the trigger mechanism such that a selected one of the protrusions is engaged to the trigger mechanism whereby a selectable amount of compression of the spring mechanism is achieved;
        a capsule chamber coupled to the barrel for holding the plurality of capsules and in communication with an interior of the barrel such that one of the capsules is delivered to the barrel such that the capsule abuts the slide member when the slide member is moved into engagement with the trigger mechanism;
        the trigger mechanism being depressable whereby the trigger mechanism disengages the slide member whereby the capsule is propelled out of the barrel.

2. A medication delivery system for medicating an animal having skin, the medication delivery system comprising:
    a pellet gun;
    a 70 caliber frangible capsule containing an animal medication in liquid form;
    the frangible capsule being positionable within the pellet gun such that the frangible capsule is ejectable from the pellet gun such that the frangible capsule breaks upon impacting the animal whereby the medication is topically delivered to the animal;
    said frangible capsule being generally spheroid for preventing implantation of said frangible capsule into the animal upon impacting the animal;
    a pellet positioned within the frangible capsule for facilitating breakage of the frangible capsule when the frangible capsule strikes a surface, the pellet further being for providing agitation of the medication within the frangible capsule to facilitate even distribution of the medication to the skin of the animal for better absorption of the medication by the animal;
    wherein the medication is mixed with a liquid, the liquid including a coloring agent, the coloring agent being adapted for marking the animal when the capsule breaks upon impacting the animal for facilitating the prevention of delivering multiple doses of medication to a single animal;
    wherein the coloring agent is chosen from the group of coloring agents consisting of an oil based paint and a water based paint, the oil based paint being for prevention of the premature removal of the medication from the skin of the animal by rain, the water based paint being for facilitating the removal of the coloring agent from the animal to prevent permanent staining of the animal;
    wherein the pellet gun is a pump action pellet gun for allowing adjustment of a propulsion force provided to the frangible capsule such that the frangible capsule will impact the animal with sufficient force to break the frangible capsule upon impact without harming the animal whereby the animal can be safely medicated from varying distances;
    wherein a color of the coloring agent is associated with a pre-determined dosage of medication for providing a visual indication of a dosage level and facilitating the prevention of overmedicating the animal;
    wherein the medication is an insecticide for the prevention of pests chosen from the group of pests including worms, flies and lice;
    wherein the pellet gun comprises
        a handle portion having a trigger mechanism;
        a barrel extending from the handle portion;
        a spring mechanism positioned within a first end of the barrel proximate the handle portion;
        a slide member having a plurality of protrusions extending therefrom, each protrusion being for engaging the trigger mechanism such that the spring mechanism is compressed;
        a slide grip coupled to the barrel for moving the slide member into engagement with the trigger mechanism such that a selected one of the protrusions is engaged to the trigger mechanism whereby a selectable amount of compression of the spring mechanism is achieved;
        a removable capsule chamber coupled to the barrel by a loop and a clip, the clip being positioned on a top of the pellet gun proximate the handle portion, the loop being positioned at an opposite end of the pellet gun, the capsule chamber being for holding the plurality of capsules within an interior of the capsule chamber, the interior of the capsule chamber being in communication with an interior of the barrel such that one of the capsules is delivered to the barrel such that the capsule abuts the slide member when the slide member is moved into engagement with the trigger mechanism;

the trigger mechanism being depressable whereby the trigger mechanism disengages the slide member whereby the capsule is propelled out of the barrel.

3. The medication delivery system of claim 2, wherein the capsule chamber further comprises a shoulder positioned on an upper surface of the capsule chamber for abutting the loop when the capsule chamber is coupled to the barrel of the pellet gun.

* * * * *